United States Patent
Fujita et al.

(10) Patent No.: US 6,433,167 B1
(45) Date of Patent: Aug. 13, 2002

(54) TRIAZOLO-1,4-DIAZEPINE COMPOUNDS AND MEDICINAL COMPOSITION CONTAINING THE SAME

(75) Inventors: Masakazu Fujita; Taketsugu Seki; Haruaki Inada; Tetsuro Sano, all of Omiya (JP)

(73) Assignee: Nikken Chemicals Co., Ltd., Tokyo (JP)

(*) Notice: Subject to any disclaimer, the term of this patent is extended or adjusted under 35 U.S.C. 154(b) by 0 days.

(21) Appl. No.: 09/446,736
(22) PCT Filed: Jun. 23, 1998
(86) PCT No.: PCT/jP98/02783
§ 371 (c)(1), (2), (4) Date: Dec. 23, 1999
(87) PCT Pub. No.: WO98/58930
PCT Pub. Date: Dec. 30, 1998

(30) Foreign Application Priority Data

Jun. 25, 1997 (JP) ............................................ 9-183229

(51) Int. Cl.⁷ ........................................ A61K 31/5513
(52) U.S. Cl. ........................................ 540/555; 514/219
(58) Field of Search ............................ 514/219; 540/555

(56) References Cited

U.S. PATENT DOCUMENTS

| 5,049,560 A | 9/1991 | Esanu et al. ............... 514/219 |
| 5,753,647 A | 5/1998 | Weber et al. ............... 514/219 |

FOREIGN PATENT DOCUMENTS

| EP | 0 503 471 | 9/1992 |
| EP | 0 606 103 | 7/1994 |
| EP | 0 624 588 | 11/1994 |
| GB | 2 229 723 | 10/1990 |
| JP | 02049787 | 2/1990 |
| JP | 02191281 | 7/1990 |
| JP | 2-256682 | 10/1990 |
| JP | 04226993 | 8/1992 |
| JP | 08040904 | 2/1996 |

OTHER PUBLICATIONS

Saeed et al., Anti–inflammatory and anti–thrombotic effects of quinidine, Medical Science Research, vol. 27, pp. 621–624, 1999.*

* cited by examiner

*Primary Examiner*—Brenda Coleman
(74) *Attorney, Agent, or Firm*—Christie, Parker & Hale, LLP

(57) ABSTRACT

A triazolo-1,4-diazepine compound having the formula (I):

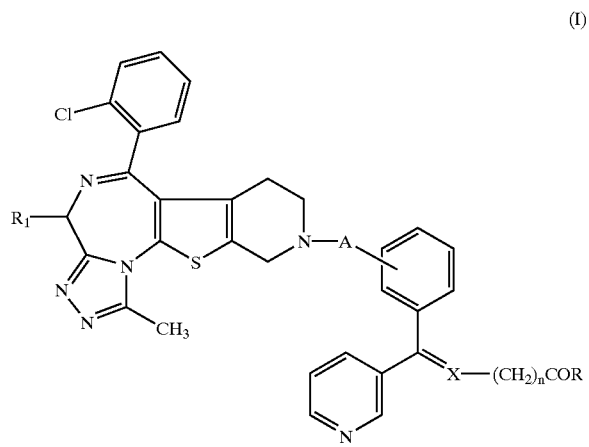

(I)

wherein A represents CO, CO—B, or B, B represents a $C_1$ to $C_6$ alkylene group or a $C_2$ to $C_6$ alkylene group having an oxygen atom interposed in the middle thereof, X represents N—O or CH, n represents an integer of 2 to 6, R represents a hydroxyl group, a $C_1$ to $C_6$ lower alkyloxy group or a $C_1$ to $C_6$ lower alkylamino group, provided that these groups may be substituted with an N,N-dimethylamino group, an N,N-diethylamino group, a phenyl group, or a heterocyclic group, and $R_1$ represents a hydrogen atom or a $C_1$ to $C_3$ lower alkyl group having both a PAF antagonistic action and a thromboxane synthesis inhibiting action, and a pharmaceutical composition containing the same as an active ingredient.

5 Claims, No Drawings

TRIAZOLO-1,4-DIAZEPINE COMPOUNDS AND MEDICINAL COMPOSITION CONTAINING THE SAME

CROSS-REFERENCE TO RELATED APPLICATION

This application is a national stage entry under 35 U.S.C. §371 of PCT/JP98/02783, filed Jun. 23, 1998.

TECHNICAL FIELD

The present invention relates to a novel triazolo-1,4-diazepine compound having a platelet activating factor (PAF) antagonistic action and a thromboxane $A_2$ ($TxA_2$) synthesis inhibiting action and a pharmaceutical composition, etc. having said compound or its hydrate or its pharmaceutically acceptable salt as an active ingredient.

BACKGROUND ART

PAF and $TxA_2$ interact with each other and are involved in various allergic, inflammatory, and hypersecretory diseases such as asthma, arthritis, rhinitis, bronchitis and urticaria obliterative, or circulatory ischemic diseases obstructive thrombotic diseases, arteriosclerosis, pulmonary hypertension, and further gastric ulcer, psoriasis, etc. and other conditions. Accordingly, in the treatment of these diseases, a higher therapeutic effect can be expected from simultaneously suppressing rather than individually suppressing the actions of PAF or $TxA_2$.

In the past, as a compound simultaneously suppressing the actions of PAF and $TxA_2$, there has been known the 1,4-dihydropyridine compound disclosed in Japanese Unexamined Patent Publication (Kokai) No. 8-40904.

On the other hand, the fact that a 1,4-diazepine compound has an anti-PAF action is described in, for example, Japanese Unexamined Patent Publication (Kokai) Nos. 2-49787, 2-191281, 2-256682, etc. However, these compounds do not have the action of simultaneously suppressing the actions of PAF and $TxA_2$.

DISCLOSURE OF THE INVENTION

In view of the above circumstances, an object of the present invention is to provide a 1,4-diazepine compound which simultaneously suppresses the actions of PAF and $TxA_2$.

The present inventors synthesized triazolo-1,4-diazepine compounds having various substituent groups and engaged in repeated studies on the actions of the compounds and, as a result, found that a triazolo-1,4-diazepine compound having the following formula (I) possesses a superior PAF antagonistic action and thromboxane $A_2$ synthesis inhibiting action, whereby the present invention has been completed.

That is, in accordance with the present invention, there is provided a triazolo-1,4-diazepine compound having the formula (I):

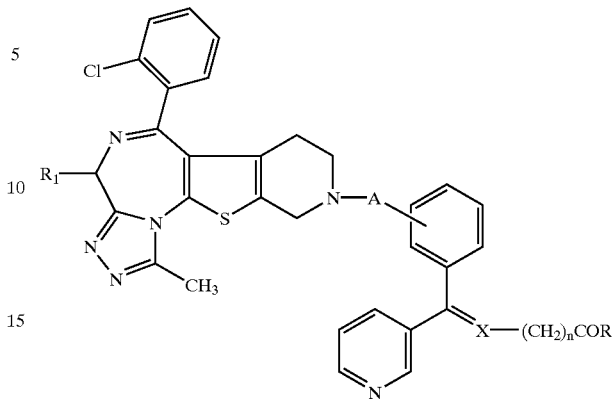

wherein A represents CO, CO—B, or B, B represents a $C_1$ to $C_6$ alkylene group or a $C_2$ to $C_6$ alkylene group having an oxygen atom interposed in the middle thereof, X represents N—O or CH, n represents an integer of 2 to 6, R represents a hydroxyl group, a $C_1$ to $C_6$ lower alkyloxy group or a $C_1$ to $C_6$ lower alkylamino group, provided that these groups may be substituted with an N,N-dimethylamino group, an N,N-diethylamino group, a phenyl group, or a heterocyclic group such as a pyridyl group, a morpholino group, a piperazino group, an imidazolyl group, and $R_1$ represents a hydrogen atom or a $C_1$ to $C_3$ lower alkyl group.

In accordance with the present invention, there are further provided a pharmaceutical composition containing the compound having the formula (I) or its hydrate or its pharmaceutically acceptable salt as an active ingredient, in particular an antiallergic or antiinflammatory pharmaceutical composition.

BEST MODE FOR WORKING THE INVENTION

The present invention will be explained in further detail below.

In the triazolo-1,4-diazepine compound having the formula (I), as mentioned above, A represents CO, CO—B, or B, and B represents a $C_1$ to $C_6$ alkylene group or a $C_2$ to $C_6$ alkylene group having an oxygen atom interposed in the middle thereof. Preferably, A represents CO—$CH_2$, CO—$CH_2OCH_2$, or a $C_1$ to $C_4$ alkylene group, in particular $CH_2$ (methylene group). Specifically, B is preferably a methylene group, an ethylene group, a trimethylene group, a tetramethylene group, a hexamethylene group, a group ($CH_2OCH_2$) having an oxygen atom interposed between one methylene group and another methylene group, etc. X, as mentioned before, is N—O or CH. Further, as mentioned above, n is an integer of 2 to 6, preferably 4. Further, R is a hydroxyl group, a $C_1$ to $C_6$ lower alkyloxy group, or a $C_1$ to $C_6$ lower alkylamino group. The above groups may be substituted with an N,N-dimethylamino group, an N,N-diethylamino group, a phenyl group, or a heterocyclic group such as a pyridyl group, a morpholino group, piperazino group, imidazolyl group etc. Preferably a $C_1$ to $C_3$ lower alkyloxy group (which may be substituted with an N,N-dimethylamino group, N,N-diethylamino group, pyridyl group, morpholino group, piperazino group, or imidazolyl group), particularly preferably a $C_1$ to $C_3$ lower alkyloxy group. $R_1$ is a hydrogen atom or a $C_1$ to $C_3$ lower alkyl group, preferably a methyl group.

Among the triazolo-1,4-diazepine compounds of the present invention, specific examples of particularly preferable compounds are Compound 4, Compound 6, Compound 7, Compound 9, Compound 10, and Compound 11 described in the Examples below.

Note that the compound of the present invention may optionally, form a hydrate or salt thereof. These, of course, are included in the present invention.

The compound of the present invention is produced by ordinary methods, but the representative methods among these are as follows.

(Production Method 1)

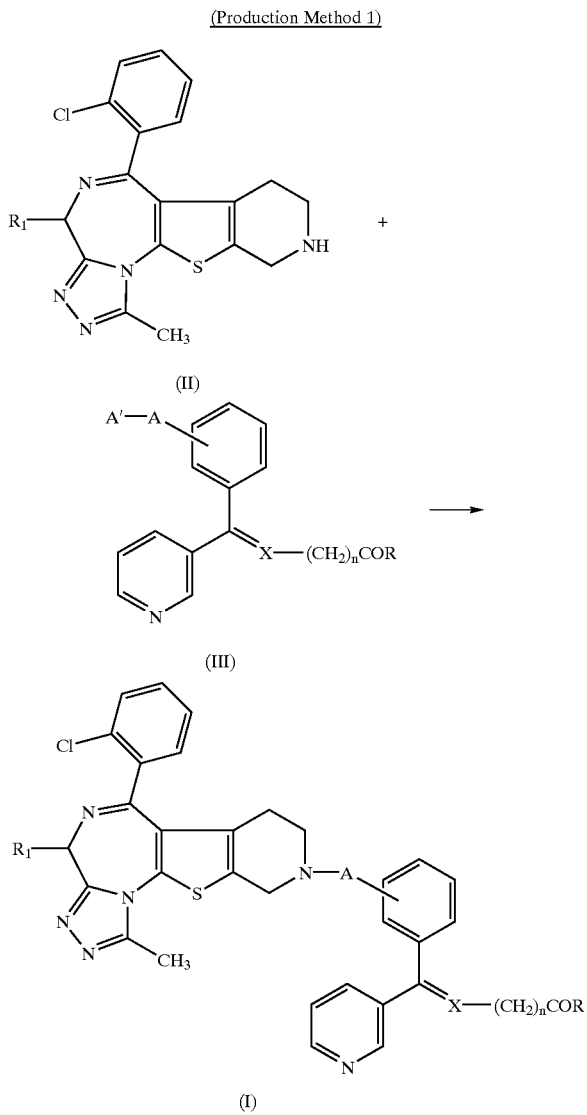

wherein, A, X, n, R, and $R_1$ are as defined above, A' represents a hydroxyl group, a halogen atom, a mesyloxy group, a tosyloxy group, etc.

That is, the desired compound having the formula (I) can be obtained by the condensation reaction between the compound of the formula (II) and the compound of the formula (III) in an ordinary method.

As the compound represented by the formula (III), an acid halide such as an acid chloride or acid bromide; an active ester such as N-hydroxybenzotriazole or N-hydroxysuccinimide; etc. a symmetric acid anhydride; a mixed acid anhydride such as an alkyl carbonic acid, methane sulfonic acid, or p-toluene sulfonic acid, etc. may be mentioned. The reaction in the case of using these compounds is carried out in the absence of a solvent or in the presence of a solvent which is not involved in the reaction such as toluene, xylene, chloroform, dichloromethane, tetrahydrofuran, or dimethylformamide, etc. under heating, for example, by a condensation reaction such as a dehalogenation reaction etc. In this case, a more preferable result is obtained if the reaction is carried out in the presence of an inorganic salt such as sodium hydrogencarbonate, sodium carbonate, or sodium hydroxide or an organic salt such as triethylamine, pyridine, or piperazine.

When a free carboxylic acid is used as the compound of formula (III), a more preferable result is obtained, if the reaction is carried out in the presence of a condensing agent such as dicyclohexylcarbodimide or 1,1'-carbonyldiimidazole etc.

When a compound containing an alkyl group to which a halide etc. or a leaving group is bonded is used, as the compound of formula (III), the reaction is carried out using an inorganic salt such as potassium carbonate, sodium carbonate, calcium carbonate, sodium hydroxide, a hydrogenated alkali metal such as sodium hydride or potassium hydride, or an organic salt such as triethylamine, pyridine, or piperazine, optionally, in the presence of a catalyst such as a crown ether etc. In particular, the reaction is suitably carried out with sodium hydride in dimethylformamide in the presence of a crown ether catalyst.

(Production Method 2)

The starting material (III) usable in the above production method 1 may be produced by, for example, the following method A or method B:

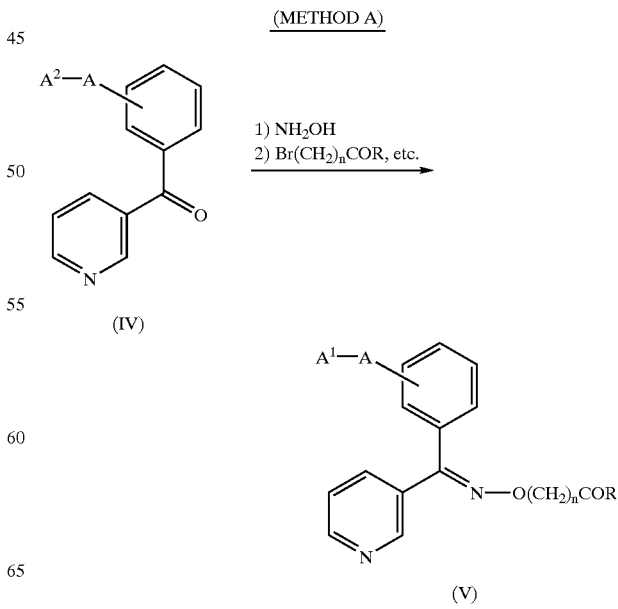

-continued
(METHOD B)

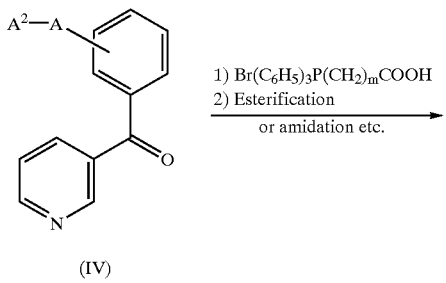

(IV)

1) $Br(C_6H_5)_3P(CH_2)_mCOOH$
2) Esterification or amidation etc.

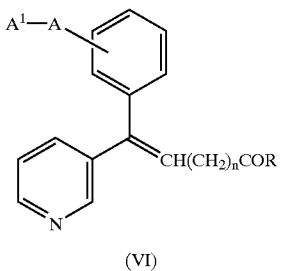

(VI)

wherein, A, $A^1$, n, and R are the same as defined above, $A^2$ represents a group stable under alkaline conditions such as a t-butyldiphenylsilyloxy group or t-butyldimethylsilyloxy group or a group the same as $A^1$, and m is an integer of 3 to 7.

The above steps will be explained in brief below.

(Method A)

The compound of formula (IV) is allowed to react with hydroxylamine in an ordinary method to form an oxime, then is allowed to react, in an inert solvent, in the presence of a base, with a halogenated alkanoic acid ester such as ethyl 5-bromovalerate or a halogenated alkanoic acid amide such as N-propyl 5-bromovaleramide, etc. then the blocking group of the hydroxyl group is removed and, if desired, a treatment such as halogenation, tosylation, mesylation etc. is carried out to introduce a leaving group or oxidize the alcohol to obtain the compound of formula (V).

The preferable base usable in this reaction is a hydrogenated alkali metal or hydrogenated alkali earth metal such as sodium hydride or calcium hydride.

(Method B)

The compound of formula (IV) is allowed to react with triphenylphosphonium bromide, etc. in a solvent in the presence of a base to form a corresponding carboxylic acid, then if desired, is esterified or amidated, then the blocking group for the hydroxyl group is removed and, if desired, is treated by halogenation, tosylation, mesylation, etc., to introduce a leaving group or to oxidize the alcohol, whereby the compound of formula (VI) is formed.

The base usable in this reaction is, for example, n-butyllithium, sodium hydride, potassium t-butoxide, etc. The solvent usable in this reaction is, for example, ether, tetrahydrofuran, dimethylformamide, dimethylsulfoxide, t-butanol, or mixed solvents thereof. The reaction is preferably carried out under an atmosphere of a dry inert gas, for example, nitrogen gas or argon gas. The reaction temperature is preferably $-10°$ C. to 80° C., more preferably 60° C. to 70° C.

Further, the compound having the formula (I) may be produced from the compound of formula (II) and the compound of formula (IV) by reacting these compounds in the similar method to the above production method 1 and then the resulting compound is treated in the same way as the method A or the method B.

The compounds having formula (I) obtained by these methods may then be processed by a known processing means, for example, extraction, chromatography, recrystallization, etc. to be isolated and purified.

The compound of the formula (I) according to the present invention has an asymmetric carbon atom, and therefore, has optical isomers. The present invention includes any optical isomers and mixtures of isomers. Further, in the present invention, there are geometrical isomers, in addition to optical isomers. The present invention also includes all of these isomers and mixtures thereof. Further, the mixtures of isomers may be separated into the individual isomers, if desired, by a fractional crystallization method or chromatography etc.

The compound according to the present invention has a PAF antagonistic action and thromboxane synthesis inhibiting action, and therefore, is useful as an agent for the treatment of allergic diseases, inflammatory diseases, hypersecretory diseases, ischemic diseases, obliterative thrombotic diseases, arteriosclerosis, pulmonary hypertension, gastric ulcer, psoriasis, etc.

The compound of the present invention may be administered by a suitable administration method such as oral or parenteral administration when used as a drug for the treatment of allergic diseases or inflammatory diseases. The form of oral administration may include, for example, tablets, granules, capsules, pills, powders, etc., and further, the form of parenteral administration may include, for example, injections, inhalants, suppositories, liquid preparations, etc. These preparations may be produced by ordinary methods from the compound of the present invention or its pharmaceutically acceptable salt and a carrier.

For example, in the case of oral administration, the preparation can be prepared into the desired form using excipients such as lactose, glucose, corn starch, etc. and sucrose, disintegrants such as calcium carboxymethylcellulose and hydroxypropylcellulose, etc. lubricants such as calcium stearate, magnesium stearate, talc, polyethylene glycol, or a hydrogenated oil, etc. binders such as hydroxypropylcellulose, hydroxypropylmethylcellulose, carboxymethylcellulose, polyvinyl alcohol, gelatin, or arabic gum, etc. humectants such as glycerol or ethylene glycol, etc. and, in addition, if necessary, surfactants, corrigents, etc. Further, in the case of a parenterally drug, diluents such as water, ethanol, glycerin, propylene glycol, polyethylene glycol, agar, or tragacanth gum etc. may be used and, in accordance with need, solubilizing agents, buffering agents, preservatives, flavors, coloring agents, etc. may be used.

When the compound of the present invention is formulated as an antiallergic, the dosage, in terms of the amount of the compound of the present invention per adult is 1 to 300 mg per day, preferably 1 to 100 mg, in the case of oral administration and 0.1 to 100 mg per day, preferably 0.5 to 30 mg, in the case of parenteral administration. The desired effect of treatment can be expected by the administration divided into one to three dosages per day.

EXAMPLES

Synthesis Examples, Preparation Examples, and Test Examples of the compound according to the present invention will be explained as Examples below, but of course the present invention is not limited to these Examples.

Below, the $^1$H NMR data shows signals using TMS as the internal standard, LAH indicates lithium aluminum hydride, HOBT indicates 1-hydroxybenzotriazole, DCC indicates dicyclohexylcarbodiimide, THF indicates tetrahydrofuran, and DMF indicates N,N-dimethylformamide.

Synthesis Examples

The Synthesis Examples of the compound of the present invention are shown below.

Example 1

(Compound 1) 6-(2-Chlorophenyl)-3-[2-[((E/Z)-4-ethoxycarbonylbutyloxyimino)(3-pyridyl)methylene]phenylcarbonyl]-8,11-dimethyl-2,3,4,5-tetrahydro-8H-pyrido[4',3':4,5]thieno[3,2-f][1,2,4]triazolo[4,3-a][1,4]diazepine

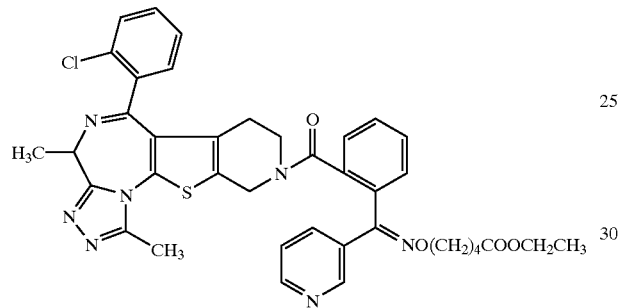

(1) Synthesis of 6-(2-Chlorophenyl)-3-[2-(3-pyridylcarbonyl)phenylcarbonyl]-8,11-dimethyl-2,3,4,5-tetrahydro-8H-pyrido[4',3':4,5]thieno[3,2-f][1,2,4]triazolo[4,3-a][1,4]diazepine

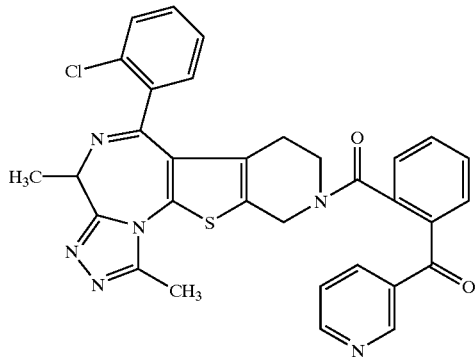

1 g of 6-(2-chlorophenyl)-8,11-dimethyl-2,3,4,5-tetrahydro-8H-pyrido[4',3':4,5]thieno[3,2-f][1,2,4]triazolo[4,3-a][1,4]diazepine and 650 mg of 3-(2-carboxyphenylcarbonyl)pyridine were suspended in 30 ml of THF, then 390 mg of HOBT was added, and the mixture was stirred under ice cooling. Under the same reaction conditions, 590 mg of DCC was added and the mixture was stirred for 1 hour. Further, the reaction solution was stirred for 1 hour at room temperature, then an aqueous saturated solution of sodium hydrogencarbonate was added thereto and the resultant mixture was extracted with chloroform. The organic layer was dried over sodium sulfate, filtered, and concentrated in vacuo, then the residue obtained was purified by silica gel column chromatography (eluent: chloroform:methanol=30:1) to obtain the desired compound in an amount of 1.3 g.

(2) To 1 g of the compound obtained at (1) was added, a solution of 140 mg of hydroxylamine hydrochloride in 20 ml of ethanol and 1 ml of pyridine. The mixture was heated to reflux for 2 hours, then was dried in vacuo. Then, 30 ml of DMF was added thereto, 130 mg of 60% sodium hydride was added gradually under ice cooling. The reaction solution was stirred for 1 hour at room temperature, then 690 mg of ethyl 5-bromovalerate was added, the mixture was stirred under the same reaction conditions for 2 hours, then the mixture was diluted with water and extracted with ethyl acetate. The organic layer was washed with water, then dried over magnesium sulfate, filtered, and concentrated in vacuo. The residue obtained was purified by silica gel column chromatography (eluent: chloroform:methanol=30:1) to obtain the desired compound (Compound 1) in an amount of 100 mg.

$^1$H-NMR (CDCl$_3$)δ; 1.2–1.3 (m, 3H), 1.4–2.3 (m, 12H), 2.69 (s, 3H), 3.3–5.2 (m, 8H), 7.2–7.8 (m, 10H), 8.6–8.7 (m, 2H).

Example 2

(Compound 2) 6-(2-Chlorophenyl)-3-[3-[((E/Z)-4-ethoxycarbonylbutyloxyimino)(3-pyridyl)methyl]phenylcarbonyl]-8,11-dimethyl-2,3,4,5-tetrahydro-8H-pyrido[4',3':4,5]thieno[3,2-f][1,2,4]triazolo[4,3-a][1,4]diazepine (1) Synthesis of Ethyl(E/Z)-5-[[3-(t-butyldiphenylsilyloxymethyl)phenyl-3-pyridyl]methyleneaminooxy]pentanecarbonate 100 ml of ethanol and 5 ml of pyridine were added to 16.6 g of [3-(t-butyldiphenylsilyloxymethyl)phenyl](3-pyridyl)ketone and 5.1 g of hydroxylamine hydrochloride. The mixture was heated to reflux for 2 hours, then dried in vacuo. 100 ml of DMF was added and 2.9 g of 60% sodium hydride was gradually added under ice cooling. The mixture was stirred at room temperature for 1 hour, then 15.3 g of ethyl 5-bromovalerate was added and the mixture was then stirred under the same reaction conditions for 2 hours. This was diluted by water, then extracted with ethyl acetate, and the resultant mixture was washed with water, then dried over magnesium sulfate and concentrated in vacuo to obtain the desired compound in an amount of 29.0 g.

(2) Synthesis of Ethyl(E/Z)-5-[[[3-(hydroxymethyl)phenyl-3-pyridyl]methylene]aminooxy]pentanecarbonate 19 g of tetrabutylammonium fluoride hydrate was added to 150 ml of a THF solution of 29 g of the compound obtained at (1). The mixture was stirred at room temperature for 2 hours. After the reaction was completed, water and ethyl acetate were added for extraction of the product. The organic layer was dried over magnesium sulfate, then was filtered and concentrated in vacuo, and the residue obtained was purified by silica gel column chromatography (eluent: chloroform:methanol=50:1) to obtain the desired compound in an amount of 14.7 g.

(3) Synthesis of Ethyl(E/Z)-5-[[(3-carboxyphenyl-3-pyridyl)methylene]aminooxy]pentanecarbonate To 20 ml of a 90% acetone aqueous solution of 8.3 g of the compound obtained at (2) was added 7.3 g of potassium permanganate. The mixture was stirred at room temperature for 30 minutes. After the reaction was completed, methanol was added and the mixture was stirred for 30 minutes, then the solid was obtained by filtration and washed with acetone. The filtrate was concentrated in vacuo, then water and 1N hydrochloric acid were added to adjust the pH thereof to 5.5, then ethyl acetate was added to extract the product. The organic layer was dried over magnesium sulfate, then filtered and concentrated in vacuo, then the residue obtained was purified by silica gel column chromatography (eluent:chloroform:methanol=30:1→10:1) to obtain the target compound in an amount of 4.6 g.

(4) The compound obtained at (3) was used and a method similar to that of example 1(1) was followed to produce the desired compound (Compound 2).

$^1$H-NMR (CDCl$_3$)δ; 1.2–1.3 (m, 3H), 1.4–1.8 (m, 6H), 2.13 (d, 3H, J=6.8 Hz), 2.31 (t, 2H, J=7.6 Hz), 2.69 (s, 3H), 3.3–3.7 (m, 3H), 4.1–4.2 (m, 2H), 4.21 (t, 2H, J=6.4 Hz), 4.29 (q, 1H, J=6.8 Hz), 4.5–4.8 (m, 2H), 5.0–5.2 (m, 1H), 7.2–7.8 (m, 10H), 8.5–8.7 (m, 2H).

Example 3

(Compound 3) 6-(2-Chlorophenyl)-3-[4-[((E/Z)-4-ethoxycarbonylbutyloxyimino)(3-pyridyl)methyl]phenylcarbonyl]-8,11-dimethyl-2,3,4,5-tetrahydro-8H-pyrido[4',1,3':4,5]thieno[3,2-f][1,2,4]triazolo[4,3-a][1,4]diazepine This was prepared by the same method as in Example 2.

$^1$H-NMR (CDCl$_3$)δ; 1.2–1.3 (m, 3H), 1.6–2.4 (m, 12H), 2.69 (s, 3H), 3.3–5.2 (m, 8H), 7.2–7.5,(m, 9H), 7.69, 7.81 (each d, together 1H, J=8.0 Hz), 8.6–8.7 (m, 2H).

Example 4

(Compound 4) 6-(2-Chlorophenyl)-3-[4-[((E/Z)-4-ethoxycarbonylbutyloxyimino)(3-pyridyl)methyl]phenylmethylcarbonyl]-8,11-dimethyl-2,3,4,5-tetrahydro-8H-pyrido[4',3':4,5]thieno[3,2-f](1,2,4]triazolo[4,3-a][1,4]diazepine This was prepared by the same method as in Example 1 using 3-(4-carboxymethylphenylcarbonyl)pyridine, instead of 3-(2-carboxyphenylcarbonyl)pyridine.

$^1$H-NMR (CDCl$_3$)δ; 1.25 (t, 3H, J=6.8 Hz), 1.6–2.5 (m, 12H), 2.69 (s, 3H), 3.3–5.3 (m, 10H), 6.8–7.7 (m, 9H),7.70, 7.82 (each d, together 1H, J=7.6 Hz), 8.6–8.7 (m, 2H).

Example 5

(Compound 5) 6-(2-Chlorophenyl)-3-[3-[3-[((E/Z)-4-ethoxycarbonylbutyloxyimino)(3-pyridyl)methyl]phenyl]propylcarbonyl]-8,11-dimethyl-2,3,4,5-tetrahydro-8H-pyrido[4',3':4,5]thieno[3,2-f][1,2,4]triazolo[4,3-a][1,4]diazepine (1) Synthesis of 4-(3-Bromophenyl)butanol 3-bromobenzaldehyde and 2-carboxyethyltriphenylphosphonium bromide were reacted to synthesize 4-(3-bromophenyl)-3-butenoic acid, then this compound was esterified and then reduced to synthesize the desired compound.

(2) Synthesis of 4-[3-(3-Pyridylcarbonyl)phenyl]butyric Acid 4-(3-bromophenyl)butanol and 3-pyridylaldehyde were reacted to synthesize 4-[3-(3-pyridylcarbonyl)phenyl]butanol, then the resultant product was oxidized by a similar method as in Example 2(3) to synthesize the desired compound.

(3) The same method was used as in Example 1 using the compound obtained in (2) to synthesize the desired compound (Compound 5).

$^1$H-NMR (CDCl$_3$)δ; 1.24 (t, 3H, J=6.8 Hz), 1.6–1.8 (m, 10H), 2.0–2.1 (m, 3H), 2.30 (t, 3H, J=7.6 Hz), 2.69 (s, 3H), 3.3–5.2 (m, 10H), 7.2–7.7 (m, 10H), 8.5–8.7 (m, 2H).

Example 6

(Compound 6) 6-(2-Chlorophenyl)-3-[4-[((E/Z)-4-ethoxycarbonylbutyloxyimino)(3-pyridyl)methyl]phenylmethyloxymethylcarbonyl]-8,11-dimethyl-2,3,4,5-tetrahydro-8H-pyrido[4',3':4,5]thieno[3,2-f][1,2,4]triazolo[4,3-a][1,4]diazepine (1) Synthesis of 3-[4-(Ethoxycarbonylmethyloxymethyl)phenylcarbonyl]pyridine 150 mg of 60% sodium hydride was gradually added to 10 ml of a DMF solution of 666 mg of 3-[4-(hydroxymethyl)phenylcarbonyl]pyridine under ice cooling. The reaction solution was stirred at room temperature for 1 hour, then 0.4 ml of 2-bromoethyl acetate was added and the mixture was stirred under the same reaction conditions for 3 hours. After the reaction was completed, the reactive product was diluted with water, extracted with ethyl acetate, and the resultant product was washed with brine, then dried over magnesium sulfate, filtered, and concentrated in vacuo to obtain the desired compound in an amount of 336 mg.

(2) Synthesis of 3-[4-(carboxymethyloxymethyl)phenylcarbonyl]pyridine 10 ml of a 0.5M sodium hydroxide aqueous solution and 5 ml of methanol were added to 336 mg of the compound obtained at (1). The mixture was stirred at room temperature for 1 hour. After the reaction was completed, the reaction mixture was concentrated and 1N hydrochloric acid was added to adjust the pH thereof to 4. Thus, the precipitated solid was obtained by filtration and washed with water to obtain the desired compound in an amount of 278 mg.

(3) The same method as in Example 1 was used to produce the desired compound (Compound 6).

$^1$H-NMR (CDCl$_3$)δ; 1.2–1.3 (m, 3H), 1.5–2.9 (m, 18H), 3.3–5.2 (m, 9H), 6.8–7.9 (m, 10H), 8.6–8.7 (m, 2H).

Example 7

(Compound 7) 6-(2-Chlorophenyl)-3-[3-[((E/Z)-4-ethoxycarbonylbutyloxyimino)(3-pyridyl)methyl]phenylmethyl]-8,11-dimethyl-2,3,4,5-tetrahydro-8H-pyrido[4',3':4,5]thieno[3,2-f][1,2,4]triazolo[4,3-a][1,4]diazepine (1) Synthesis of Ethyl(E/Z)-5-[[(3-pyridyl-3-methanesulfonyloxymethylphenyl)methylene]aminooxy]pentanecarbonate To 10 ml of a dichloromethane solution of 1 g of the ethyl(E/Z)-5-[[(3-pyridyl-3-hydroxymethylphenyl)methylene]aminooxy]pentanecarbonate prepared by the same method as in Example 2, 0.4 g of triethylamine was added. 0.26 ml of mesyl chloride was dropwise added in an argon stream under ice cooling. The resultant mixture was stirred at room temperature for 1 hour, then an aqueous saturated solution of sodium hydrogencarbonate was added, the organic layer was separated, then the layer was dried over sodium sulfate and was concentrated in vacuo to obtain the desired compound in an amount of 1.2 g.

(2) To 20 ml of a DMF solution of 1.5 g of 6-(2-chlorophenyl)-8,11-dimethyl-2,3,4,5-tetrahydro-8H-pyrido[4',3':4,5]thieno[3,2-f][1,2,4]triazolo[4,3-a][1,4]diazepine and 2.0 g of the compound obtained at (1) 1.3 g of potassium carbonate and 619 mg of 18-crown-6 were added. The mixture was stirred at 70° C. for 2 hours. After the reaction was completed, water and ethyl acetate were added for extraction. The organic layer was washed with brine, then was dried over magnesium sulfate, concentrated in vacuo, and purified by silica gel column chromatography (eluent: chloroform:methanol=30:1) to obtain the desired compound (Compound 7) in an amount of 930 mg.

$^1$H-NMR (CDCl$_3$)δ; 1.24 (t, 3H), 1.6–1.9 (m, 6H), 2.1–2.2 (m, 3H), 2.32 (t, 2H),2.67 (d, 3H), 3.1–4.1 (m, 3H), 4.11 (q, 2H), 4.22 (q, 2H), 4.30 (q, 1H), 4.4–5.3 (m, 3H), 7.2–7.6 (m, 9H), 7.71, 7.84 (each d, together 1H), 8.6–8.7 (m, 2H).

Example 8

(Compound 8) 6-(2-Chlorophenyl)-3-[3-[((E/Z)-4-carboxydibutyloxyimino)(3-pyridyl)methyl]phenylmethyl]-8,11-dimethyl-2,3,4,5-tetrahydro-8H-pyrido[4',3':4,5]thieno[3,2-f][1,2,4]triazolo[4,3-a][1,4]diazepine 2 ml of 1M sodium hydroxide and 2 ml of methanol were added to 470 mg of Compound 7, then the mixture was stirred at room temperature for 1 hour. After the reaction was completed, 1N hydrochloric acid was dropwise added under ice cooling to adjust the pH thereof to 5.5. Ethyl acetate was added to this to extract the product, then the extract was dried over magnesium sulfate, was concentrated in vacuo, and purified by silica gel column chromatography (eluent: chloroform:methanol=30:1) to obtain the desired compound (Compound 8) in an amount of 145 mg.

$^1$H-NMR (CDCl$_3$)δ; 1.7–1.8 (m, 6H), 2.12 (d, 3H), 2.36 (t, 2H), 2.68 (d, 3H), 3.1–4.0 (m, 3H), 4.23 (t, 2H), 4.28 (q, 1H), 4.3–5.3 (m, 3H), 7.2–7.7 (m, 9H), 7.72, 7.83 (each d, together 1H), 8.5–8.7 (m, 2H).

Example 9

(Compound 9) 6-(2-Chlorophenyl)-3-[4-[((E/Z)-4-ethoxycarbonylbutyloxyimino)(3-pyridyl)methyl]-phenylmethyl]-8,11-dimethyl-2,3,4,5-tetrahydro-8H-pyrido[4',3':4,5]thieno[3,2-f][1,2,4]triazolo[4,3-a][1,4]diazepine This was prepared by the same method as in Example 7.

$^1$H-NMR (CDCl$_3$)δ; 1.24 (t, 3H), 1.6–2.7 (m, 16H), 3.5–3.8 (m, 4H), 4.13 (q, 2H), 4.1–4.3 (m, 3H), 7.2–7.5 (m, 9H), 7.72, 7.84 (each d, together 1H), 8.5–8.7 (m, 2H).

Example 10

(Compound 10) 6-(2-Chlorophenyl)-3-[3-[((E/Z)-5-ethoxycarbonylpentylidene)(3-pyridyl)methyl]phenylmethyl]-8,11-dimethyl-2,3,4,5-tetrahydro-8H-pyrido[4',3':4,5]thieno[3,2-f][1,2,4]triazolo[4,3-a][1,4]diazepine This was prepared by the same method as in Example 7(2).

$^1$H-NMR (CDCl$_3$)δ; 1.2–1.3 (m, 3H), 1.4–1.9 (m, 4H), 1.9–2.6 (m, 11H), 2.67 (d, 3H), 3.1–4.0 (m, 3H), 4.12 (q, 2H), 4.29 (q, 1H), 4.3–5.3 (m, 1H), 6.0–6.2 (m, 1H), 7.0–7.5 (m, 10H), 8.4–8.6 (m, 2H).

Example 11

(Compound 11) 6-(2-Chlorophenyl)-3-[4-[((E/Z)-5-ethoxycarbonylpentylidene)(3-pyridyl)methyl]phenylmethyl]-8,11-dimethyl-2,3,4,5-tetrahydro-8H-pyrido[4',3':4,5]thieno[3,2-f][1,2,4]triazolo[4,3-a][1,4]diazepine This was prepared by the same method as in Example 7.

$^1$H-NMR (CDCl$_3$)δ; 1.2–1.3 (m, 3H), 1.4–1.9 (m, 4H), 1.9–2.8 (m, 14H), 3.1–5.2 (m, 7H), 6.0–6.2 (m, 1H), 7.1–7.5 (m, 10H), 8.44 (s, 1H), 8.56 (d, 1H)

Example 12

(Compound 12) 6-(2-Chlorophenyl)-3-[4-[3-[((E/Z)-4-ethoxycarbonylbutyloxyimino)(3-pyridyl)methyl]phenyl]butyl]-8,11-dimethyl-2,3,4,5-tetrahydro-8H-pyrido[4',3':4,5]thieno[3,2-f][1,2,4]triazolo[4,3-a][1,4]diazepine This was prepared by the same method as in Examples 5 and 7.

$^1$H-NMR (CDCl$_3$)δ; 1.24 (t, 3H), 1.5–1.8 (m, 12H), 2.13 (d, 3H), 2.2–2.4 (m, 2H), 2.5–2.8 (m, 2H), 2.68 (s, 3H), 3.0–4.9 (m, 6H), 4.11 (q, 2H), 4.21 (t, 2H), 4.28 (q, 1H), 7.1–7.6 (m, 9H), 7.6–7.7, 7.83 (each m, d, together 1H), 8.5–8.7 (m, 2H).

Example 13

(Compound 13) 6-(2-Chlorophenyl)-3-[3-[((E/Z)-4-(2-morpholinoethoxycarbonyl)butyloxyimino)(3-pyridyl)methyl]phenylmethyl]-8,11-dimethyl-2,3,4,5-tetrahydro-8H-pyrido[4',3':4,5]thieno[3,2-f][1,2,4]triazolo[4,3-a][1,4]diazepine This was prepared by the same method as in Example 7.

$^1$H-NMR (CDCl$_3$)δ;

1.6–1.8 (m, 5H), 2.1–2.2 (m, 4H), 2.33 (t, 2H), 2.4–2.7 (m, 11H), 3.5–3.7 (m, 7H), 4.1–5.2 (m, 6H), 7.2–7.4 (m, 9H), 7.6–7.8 (m, 1H), 8.5–8.6 (m, 2H).

Example 14

(Compound 14) 6-(2-Chlorophenyl)-3-[3-[((E/Z)-4-benzyloxycarbonylbutyloxyimino)(3-pyridyl)methyl]phenylmethyl]-8,11-dimethyl-2,3,4,5-tetrahydro-8H-pyrido[4',3':4,5]thieno[3,2-f][1,2,4]triazolo[4,3-a][1,4]diazepine This was prepared by the same method as in Example 7.

$^1$H-NMR (CDCl$_3$)δ; 1.6–1.7 (m, 5H), 2.1–2.2 (m, 4H), 2.37 (t, 2H), 2.49–2.52 (m, 1H), 2.65–2.68 (m, 4H), 3.1–4.0 (m, 3H), 4.2–4.3 (m, 3H), 4.4–5.2 (m, 1H), 5.09 (d, 2H), 7.2–7.4 (m, 14H), 7.82, 7.68 (each d, together 1H), 8.5–8.6 (m, 2H).

Example 15

(Compound 15) 6-(2-Chlorophenyl)-3-[3-[((E/Z)-4-propylaminocarbonylbutyloxyimino)(3-pyridyl)methyl]phenylmethyl]-8,11-dimethyl-2,3,4,5-tetrahydro-8H-pyrido[4',3':4,5]thieno[3,2-f][1,2,4]triazolo[4,3-a])[1,4]diazepine This was prepared by the same method as in Example 7.

$^1$H-NMR (CDCl$_3$)δ; 0.89 (t, 3H), 1.4–1.7 (m, 7H), 2.1–2.6 (m, 6H), 2.5–2.7 (m, 5H), 3.1–3.2 (m, 2H)., 3.4–4.0 (m, 3H), 4.2–4.3 (m, 3H), 4.4–5.5 (m, 2H), 7.2–7.4 (m, 9H), 7.00, 7.82 (each d, together 1H), 8.5–8.6 (m, 2H).

Example 16

(Compound 16) 6-(2-Chlorophenyl)-3-[3-[((E/Z)-4-(3-(3-pyridyl)propyloxycarbonyl)butyloxyimino)(3-pyridyl)methyl]phenylmethyl]-8,11-dimethyl-2,3,4,5-tetrahydro-8H-pyrido[4',3':4,5]thieno[3,2-f][1,2,4]triazolo,[4,3-a][1,4]diazepine This was prepared by the same method as in Example 7.

$^1$H-NMR (CDCl$_3$)δ; 1.68–1.73 (m, 5H), 1.9–2.0 (m, 2H), 2.1–2.2 (m, 1H), 2.11 (d, 3H), 2.32 (t, 2H), 2.48–2.55 (m, 1H), 2.66–2.74 (m, 3H), 2.67 (d, 3H), 3.5–3.7 (m, 3H), 4.08 (q, 2H), 4.1–4.2 (m, 2H), 4.27 (q, 1H), 4.3–5.2 (m, 1H), 7.2–7.5 (m, 11H), 7.6–7.8 (m, 1H), 8.4–8.6 (m, 4H).

The structures of the compounds obtained in the above examples are shown in the following Table I.

TABLE I

| Compound | A | Bonding position of A | X | R |
|---|---|---|---|---|
| Compound 1 | CO | ortho | N—O | —OC$_2$H$_5$ |
| Compound 2 | CO | meta | N—O | —OC$_2$H$_5$ |
| Compound 3 | CO | para | N—O | —OC$_2$H$_5$ |
| Compound 4 | COCH$_2$ | para | N—O | —OC$_2$H$_5$ |
| Compound 5 | CO(CH$_2$)$_3$ | meta | N—O | —OC$_2$H$_5$ |
| Compound 6 | COCH$_2$OCH$_2$ | para | N—O | —OC$_2$H$_5$ |
| Compound 7 | CH$_2$ | meta | N—O | —OC$_2$H$_5$ |
| Compound 8 | CH$_2$ | meta | N—O | —OH |
| Compound 9 | CH$_2$ | para | N—O | —OC$_2$H$_5$ |
| Compound 10 | CH$_2$ | meta | CH | —OC$_2$H$_5$ |
| Compound 11 | CH$_2$ | para | CH | —OC$_2$H$_5$ |
| Compound 12 | (CH$_2$)$_4$ | meta | N—O | —OC$_2$H$_5$ |
| Compound 13 | CH$_2$ | meta | N—O | —O(CH$_2$)$_2$—N(morpholine) |
| Compound 14 | CH$_2$ | meta | N—O | —OCH$_2$-phenyl |
| Compound 15 | CH$_2$ | meta | N—O | —NH—C$_3$H$_7$ |
| Compound 16 | CH$_2$ | meta | N—O | —O(CH$_2$)$_3$-pyridyl |

Preparation Example

Preparation Examples of pharmaceutical compositions according to the present invention will be explained below.

| Example 17 (Preparation of Tablet) | |
|---|---|
| Compound of invention (Compound 1) | 250 g |
| Lactose | 620 g |
| Corn starch | 400 g |
| Hydroxypropylcellulose | 20 g |
| Magnesium stearate | 10 g |

The above compound of the present invention, lactose, and corn starch were mixed until the mixture became homogeneous, then a 5 W/V % ethanol solution of hydroxypropylcellulose was added and the resultant mixture was kneaded and granulated. The resultant product was passed through a 16 mesh sieve to obtain standard sized granules, then tableted by an ordinary method to obtain the desired tablets having a weight per tablet of 130 mg, a diameter of 7 mm, and a content of active ingredient of 25 mg.

TEST EXAMPLES

Test Examples of the pharmaceutical composition of the present invention are given below.

Test Example 1

PAF Antagonistic Action Test

Japanese white rabbits (2.5 to 3.0 kg, Clean Experimental Animal Center) were used. Nine volumes of blood were taken with respect to one volume of 3.8% sodium citrate from the carotid under anesthesia by pentobarbitol. This was centrifuged at 1000 rpm and room temperature for 10 minutes. The top layer was used as the platelet rich plasma (PRP). The lower layer was further centrifuged at 3000 rpm and room temperature for 10 minutes to obtain the platelet poor plasma (PPP).

5 μl (final concentration $10^{-7}$M) of the test compound was added to 90 μl of PRP. This was incubated at 37° C. for 3 minutes, then a platelet activating factor (PAF, final concentration 17 nM) was added to cause aggregation and the aggregation reaction was measured for 5 minutes using an aggrigometer (MC Medical, PAT-606).

The test results are shown in Table II.

Test Example 2

$TxA_2$ Synthesis Inhibiting Action Test 1 ml of a buffer (20 MM Tris-HCl buffer, 1 mM EDTA, pH 7.5) containing human blood platelet microsomes (50 μg protein/ml) and the test compound (final concentration $10^{-7}$M) was agitated, then incubated at 0° C. for 30 minutes. To this was added prostaglandin $H_2$ (100 ng/2 μl). This was incubated at 23° C. for 3 minutes to cause a reaction. Next, 1M hydrochloric acid was added to make the solution acidic and stop the reaction, then this was neutralized by 1M Tris-Base and centrifuged at 3000 rpm for 20 minutes. The amount of the $TxB_2$ in the supernatant was measured by the EIA method (Cayman Co. kit).

The test results are shown in Table II. a Further, as controls, UK-74,505 having a PAF antagonistic action and OKY-046 having a $TxA_2$ synthesis inhibiting action were used.

TABLE II

| Compound tested | PAF antagonistic action Rate of suppression at $10^{-7}$ M (%) | $TxA_2$ synthesis inhibiting action Rate of suppression at $10^{-7}$ M (%) |
|---|---|---|
| Compound 1 | 82.0 | 53.0 |
| Compound 4 | 94.6 | 79.6 |
| Compound 5 | 95.5 | 40.3 |
| Compound 6 | 79.8 | 75.6 |
| Compound 7 | 94.0 | 58.2 |
| Compound 8 | 52.0 | 81.7 |
| Compound 11 | 94.2 | 83.7 |
| Control UK-74,505 | 89.0 | 0 |
| Control OKY-046 | 0 | 84.5 |

From Table II, it is clear that the compounds of the present invention have both a PAF antagonistic action and a $TxA_2$ synthesis inhibiting action.

Test Example 3

Acute Toxicity Test

The compound of the present invention used in the above Test Example 2 was orally administered to rats (three to four rats) or mice (five to eight mice). No deaths were observed at a dosage of 10 mg/kg for any of the compounds. Further, when the Compound 4 or Compound 6 were administered intravenously, no deaths were observed at a dosage of 10 mg/kg.

INDUSTRIAL APPLICABILITY

The compound according to the present invention has both a PAF antagonistic action and a $TxA_2$ synthesis inhibiting action and exhibits an action alleviating allergic diseases and inflammatory diseases etc. Further, the compound according the present invention has a low toxicity and is effective both when administered orally and parenterally, and therefore is useful as a medicinal drug for humans.

What is claimed is:

1. A triazolo-1,4-diazepine compound having the formula (I):

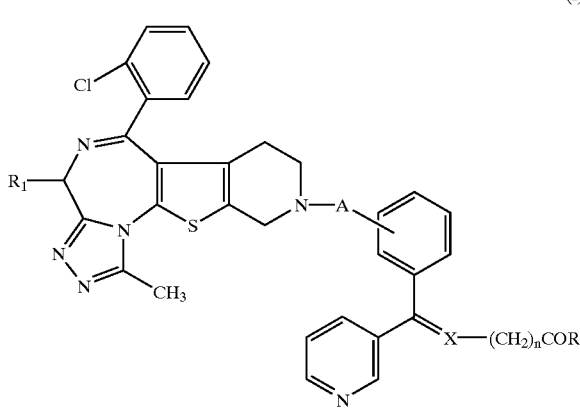

wherein:

A represents CO, CO—B or B,

B represents a $C_1$ to $C_6$ alkylene group or $C_2$ to $C_6$ alkylene group having an oxygen atom interposed in the middle thereof, X represents N—O or CH, n represents an integer of 2 to 6, R represents a hydroxyl group, a $C_1$ to $C_6$ lower alkyloxy group or a $C_1$ to $C_6$ lower alkylamino group, provided that the above-mentioned $C_1$ to $C_6$ lower alkyloxy and $C_1$ to $C_6$ lower alkylamino groups may be substituted with an N,N-dimethylamino group, an N,N-diethylamino group, a phenyl group, or a heterocyclic group selected from the group consisting of pyridyl groups, morpholino groups, piperazino groups, and imidazolyl groups, and $R_1$ represents a hydrogen atom or a $C_1$ to $C_3$ lower alkyl group.

2. A triazolo-1,4-diazepine compound as claimed in claim 1, wherein A is CO—$CH_2$, CO—$CH_2OCH_2$ or a $C_1$ to $C_4$ alkylene group, R is a $C_1$ to $C_3$ lower alkyloxy group which may be substituted with an N,N-dimethylamino group, an N,N-diethylamino group, a pyridyl group, a morpholino group, a piperazino group, or an imidazolyl group.

3. A triazolo-1,4-diazepine compound as claimed in claim 2, wherein A is a methylene group and n is 4.

4. A triazolo-1,4-diazepine compound as claimed in claim 2, wherein R is a $C_1$ to $C_3$ lower alkyloxy group.

5. A triazolo-1,4-diazepine compound as claimed in claim 3, wherein R is a $C_1$ to $C_3$ lower alkyloxy group.

* * * * *